United States Patent [19]

Seuring et al.

[11] Patent Number: 4,574,128

[45] Date of Patent: Mar. 4, 1986

[54] 5-(4-CHLORO-3-SULFAMOYLBENZOYL)-2,3-DIHYDRO-2-BENZOFURANCARBOXYLIC ACIDS AND THEIR COMPOSITIONS HAVING DIURETIC, SALURETIC AND URICOSURIC ACTIVITY

[75] Inventors: Bernhard Seuring; Hans-Jochen Lang, both of Hofheim am Taunus; Max Hropot, Flörsheim am Main; Roman Muschaweck, Frankfurt am Main, all of Fed. Rep. of Germany

[73] Assignee: Hoechst Aktiengesellschaft, Fed. Rep. of Germany

[21] Appl. No.: 610,484

[22] Filed: May 15, 1984

[30] Foreign Application Priority Data

May 17, 1983 [DE] Fed. Rep. of Germany ....... 3317884

[51] Int. Cl.[4] ..................... A61K 31/34; C07D 307/85
[52] U.S. Cl. ...................... 514/469; 549/468
[58] Field of Search .................. 549/468; 424/285; 514/469

[56] References Cited

U.S. PATENT DOCUMENTS 3,055,930  9/1982  Graf et al. ............................ 568/332
4,156,732  5/1979  Lang et al. ........................... 549/468
4,163,794  8/1979  Cragoe, Jr. et al. ................. 549/468

FOREIGN PATENT DOCUMENTS 104483   4/1984  European Pat. Off. ............. 568/333
1129478  5/1962  Fed. Rep. of Germany ...... 568/332
2630800  1/1977  Fed. Rep. of Germany ...... 549/468

OTHER PUBLICATIONS

Hoffman et al., J. Med. Chem., vol. 24, pp. 865–873, (1981).

Primary Examiner—Richard A. Schwartz
Assistant Examiner—Bernard I. Dentz
Attorney, Agent, or Firm—Finnegan, Henderson, Farabow, Garrett & Dunner

[57] ABSTRACT 5-(4-Chloro-3-sulfamoylbenzoyl)-2,3-dihydro-2-benzofurancarboxylic acids of the formula I

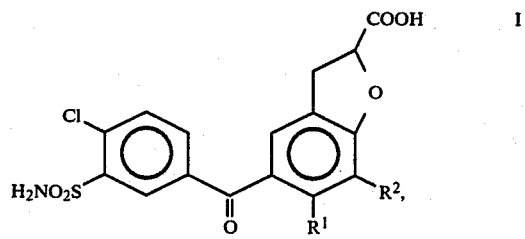

in which $R^1$ and $R^2$ are identical or different and represent hydrogen, halogen or methyl, both as racemic mixtures and in the form of their optical isomers, and their physiologically tolerated salts are described, as is their preparation. They are outstanding diuretics and saluretics with an additional uricosuric component.

3 Claims, No Drawings

5-(4-CHLORO-3-SULFAMOYLBENZOYL)-2,3-DIHYDRO-2-BENZOFURANCARBOXYLIC ACIDS AND THEIR COMPOSITIONS HAVING DIURETIC, SALURETIC AND URICOSURIC ACTIVITY

The invention relates to 5-(4-chloro-3-sulfamoylbenzoyl)-2,3-dihydro-2-benzofurancarboxylic acid derivatives of the general formula I

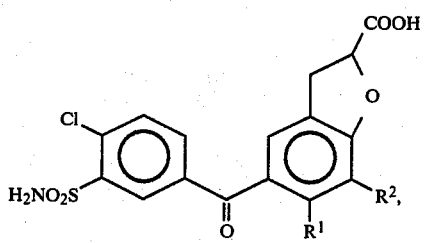

in which $R^1$ and $R^2$ are identical or different and represent hydrogen, halogen or methyl, both as racemic mixtures and in the form of the optical isomers, and their physiologically tolerated salts.

Several phenoxyacetic acid derivatives, acylated in the 4-position, and 5-aroyl-2,3-dihydro-2-benzofurancarboxylic acid derivatives having saluretic and/or uricosuric activity have already been described in the literature (cf. G. M. Shutske et al., J. Med. Chem. 25, 36–44 (1982) and literature cited there). All these compounds have a lipophilic aroyl moiety, and they act as saluretics in rats either hardly at all or only at relatively high doses. Thus, it was very surprising that the compounds of the formula I according to the invention, which are both phenoxyacetic acid derivatives and sulfonamides, exert both a uricosuric and a saluretic effect, and that, moreover, they are superior in respect of activity and/or duration of action to the abovementioned compounds, as can be demonstrated by tests on rats.

Benzophenonesulfonamide derivatives having diuretic and saluretic properties are likewise known from the literature (German Auslegeschrift No. 1,129,478), but no uricosuric or hypouricemic effects were detected for these.

The preferred compound is 5-(4-chloro-3-sulfamoylbenzoyl)-6,7-dichloro-2,3dihydro-2-benzofurancarboxylic acid, where $R^1$ and $R^2$ are Cl.

The invention also relates to a process for the preparation of compounds of the formula I, which comprises (a) reacting a carboxylic acid derivative of the formula II

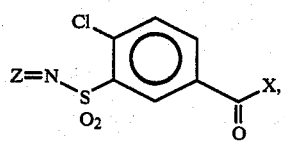

in which Z represents two hydrogens or a dimethylaminomethylene protective group, and in which X represents a leaving group, but particularly represents chlorine, with a 2,3-dihydrobenzofuran derivative of the general formula III

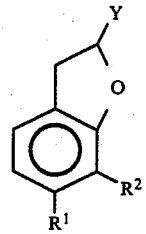

in a manner known per se by Friedel-Crafts acylation to give compounds of the general formula IV

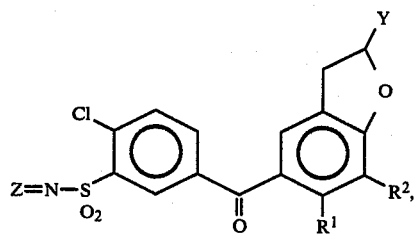

in which $R^1$, $R^2$ and Z have the abovementioned meaning, and Y represents

with $R^3$ having the meaning of H or lower alkyl with $C_1$–$C_4$, and in the case where Z denotes a dimethylaminomethylene protective group and/or $R^3$ denotes a $C_1$–$C_4$-alkyl radical, liberating by hydrolysis the compounds of the formula I according to the invention in a manner known from the literature, or (b) converting a 2,3-dihydrobenzofuran derivative of the formula V

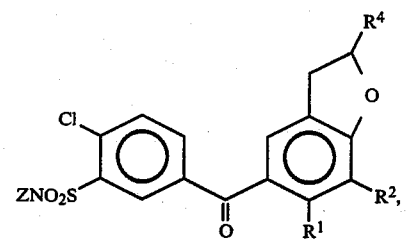

in which $R^1$, $R^2$ and Z have the indicated meanings, and $R^4$ is a $CH_2OH$ or CHO group, into the carboxylic acids of the formula I in a manner known per se using a suitable oxidizing agent.

It is possible, where appropriate, readily to convert compounds of the formula IV or V, which contain Z in the meaning of the dimethylaminomethylene protective group, in a manner known from the literature (German Offenlegungsschrift No. 2,654,795; C.A. 89, 108715 (1978)) into compounds with an unprotected sulfonamide group (Z equal to two hydrogens) and vice versa.

The compounds which are obtained by procedure (a) and have Z in the meaning of 2 hydrogen atoms and $R^3$ meaning hydrogen are identical with the compounds of the formula I according to the invention. The compounds of the formula I are obtained from the compounds of the formula IV, which are obtained by procedure (a) and in which $R^1$ and $R^2$ have the indicated meaning, $R^3$ represents lower alkyl and/or Z represents a dimethylaminomethylene group, by hydrolysis in aqueous medium in the presence of an acid or a base, preferably using lithium, sodium or potassium hydroxide or hydrochloric acid. The hydrolytic cleavage is also advantageously carried out by addition of a polar organic solvent, such as, for example, methanol, ethanol, isopropanol, acetic acid or tetrahydrofuran. The reaction is carried out in the temperature range between 0° and 120° C., advantageously being carried out between 40° and 100° C. The compounds IV are prepared in a manner known per se by reacting the dihydrobenzofuran derivatives of the formula III with carboxylic acid derivatives of the formula II in the manner of Friedel-Crafts acylation (cf. Houben-Weyl, Vol. VII/2 a, pp. 15–62, published by Georg Thieme, Stuttgart, 1973), the Friedel-Crafts catalyst which is preferably used being aluminum chloride. All the solvents customary for Friedel-Crafts acylations can be used, nitrobenzene being particularly suitable, but halogenated hydrocarbons, such as methylene chloride or 1,2-dichloroethane, can also be used with advantage. The reactions are carried out between −20° and 100° C. with 1–4 equivalents of catalyst. To avoid by-products, the reaction is advantageously carried out at temperatures below 40° C. and with stoichiometric amounts of catalyst.

The 2,3-dihydrobenzofuran derivatives of the formula III which are used are known from the literature or are obtained in analogy to procedures indicated in the literature (W. F. Hoffmann, O. W. Woltersdorf, F. C. Novello and E. J. Cragoe, J.Med. Chem. 24, 865–873 (1981)).

According to procedure (b), the hydroxymethyl or formyl group in compounds V is oxidized in a manner known per se using a suitable oxidizing agent to give the carboxyl group, and in the case where Z denotes a dimethylaminomethylene protective group, this is converted by subsequent hydrolysis, as described in detail under procedure (a), into the compounds of the formula I according to the invention. The agent which is preferably used for oxidizing the hydroxymethyl derivative V ($R^4$=CH$_2$OH) is pyridinium dichromate, the reaction advantageously being carried out with exclusion of moisture in an inert polar organic solvent, such as dimethylformamide or dimethylacetamide, between 0° and 40° C., preferably at room temperature. In principle, other oxidizing agents can also be used, such as, for example, potassium permanganate in aqueous NaOH between 10° and 40° C., or nickel peroxide in aqueous NaOH (cf. Houben-Weyl, Volume IV/1b, pp. 610 and 845 ff., published by Georg Thieme, Stuttgart, 1975).

The oxidation can also be carried out stepwise such that the hydroxymethyl compound V, with $R^4$=CH$_2$OH, is selectively oxidized to the corresponding aldehyde of the formula V ($R^4$=CHO). A favorable oxidizing agent which should be particularly mentioned is active manganese dioxide hydrate, which is preferably used in methylene chloride, acetonitrile or acetone, at room temperature, in a manner known per se (cf. Houben-Weyl, Volume 7/1, pp. 178–179 (1954)). An equally favorable oxidizing agent which can be used is ammonium hexanitratocerate(IV) in water or aqueous acetic acid, at temperatures between 60° and 80° C., in a manner known from the literature (cf. Houben-Weyl, Volume 4/1b, p. 155, published by Georg Thieme, Stuttgart, 1975)). The aldehyde derivatives V ($R^4$=CHO) thus obtained are then subjected, in a manner known from the literature, to further oxidation to give the corresponding carboxylic acids, potassium permanganate in aqueous solution at room temperature having proved to be particularly useful for this (cf. C. W. Smith et al., J. Amer. Chem. Soc. 73, 5273 (1951)). The oxidation can also advantageously be carried out with chromium(VI) oxide in a manner known per se (cf. Houben-Weyl, Volume 4/1b, p. 461, published by Georg Thieme, Stuttgart, (1974)).

The 2-hydroxymethyl-2,3-dihydrobenzofuran derivatives of the formula V used as starting components can be prepared in a manner known per se (cf. W. F. Hoffmann, O. W. Woltersdorf, F. C. Novello and E. J. Cragoe, J. Med. Chem. 24, 865 (1981)) by converting phenols of the formula VI

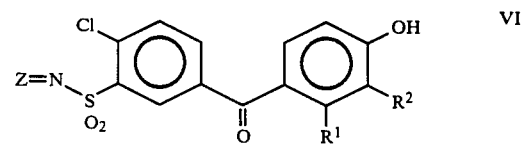

in which $R^1$ and $R^2$ have the indicated meaning, and Z is preferably a dimethylaminomethylene group, using an allyl halide in an organic solvent, such as, for example, in dimethylformamide, in the presence of a base, such as, for example, potassium carbonate, into the corresponding allyl ethers of the general formula VII

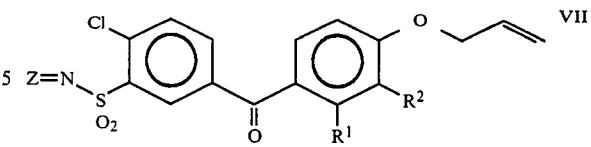

The allyl ethers VII can be converted by heat, at temperatures between 180° and 220° C., preferably in diphenyl ether as the solvent, by a Claisen rearrangement into the 2-allylphenol derivatives of the formula VIII

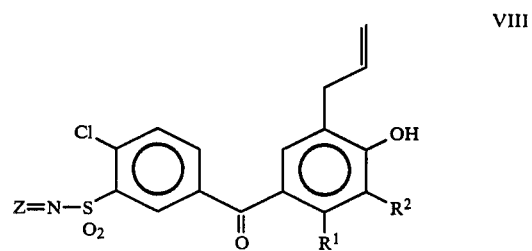

which can be converted by peroxide oxidation, preferably using an organic peracid, such as, for example, metachloroperbenzoic acid, in an inert organic solvent, such as, for example, methylene chloride, between 0° and 50° C., into the compounds of the formula V in which $R^4$ denotes a CH$_2$OH group.

The compounds of the formula I according to the invention have a center of chirality at the 2 position of the dihydrobenzofuran system. The carboxylic acids I can be converted, in a manner known from the literature, by treatment with an optically active base, such as, for example, brucine or (−)-cinchonidine, into their diastereomeric salt pairs, and these can be separated by crystallization, and from these the optical isomers of the carboxylic acids of the formula I can be liberated by treatment with a mineral acid, such as, for example, with aqueous hydrochloric acid.

According to the invention, apart from 5-(4-chloro-3-sulfamoylbenzoyl)-6,7-dichloro-2,3-dihydro-2-benzofurancarboxylic acid, which is described in the experimental example, the following compounds of the formula I according to the invention can be prepared: 5-(4-chloro-3-sulfamoylbenzoyl)-2,3-dihydro-6,7-dimethyl-2-benzofurancarboxylic acid, 5-(4-chloro-3-sulfamoylbenzoyl)-6-chloro-7-methyl-2,3-dihydro-2-benzofurancarboxylic acid, 5-(4-chloro-3-sulfamoylbenzoyl)-7-chloro-6-methyl-2,3dihydro-2-benzofurancarboxylic acid, 5-(4-chloro-3-sulfamoylbenzoyl)-6-chloro-2,3-dihydro-2-benzofurancarboxylic acid and 5-(4-chloro-3-sulfamoylbenzoyl)-7-chloro-2,3-dihydro-2-benzofurancarboxylic acid.

The compounds of the formula I according to the invention and their physiologically tolerated salts are diuretics and saluretics having an additional uricosuric component. They can be used as pharmaceuticals in human and veterinary medicine. For this purpose, they are administered orally, parenterally or intravenously in doses of 10-150 mg/kg of body weight. Alone or in combination with other substances having hypotensive, vasodilator or diuretic activity, they are not only suitable for the treatment of hypertension but are also suitable for the treatment of cardiac, renal or hepatic edema and other manifestations attributable to disturbances in the electrolyte balance. In this context, the particular importance of the abovementioned compounds is their double activity as diuretics and as uricosurics. It is known that, during diuretic treatment with known diuretics, there is in many cases an increase in the uric acid concentration in the blood of a patient. A raised level of uric acid is a serious problem in patients with gout. Moreover, a raised level of uric acid is increasingly being regarded as a risk factor for heart disease. For this reason, the diuretic effect associated with simultaneous elimination of uric acid can be regarded as a major advantage of the compounds according to the invention. The compounds can be used alone or combined with other substances having saluretic activity, even if their mode of action differs. The following may be particularly mentioned: spironolactone, triamterene, amiloride and other K+-sparing compounds. However, other, purely hypotensive, compounds are also suitable as possible partners in the combination, for example hydralazine, clonidine, reserpine and, in particular, beta-blocker substances, such as, for example, metoprolol or penbutolol.

Effective amounts of the compounds according to the invention can be administered to a patient by various means, for example orally in the form of capsules or tablets, parenterally in the form of sterile solutions or suspensions, and in some cases intravenously as sterile solutions.

The free acids, which are themselves active, can be formulated and, for reasons of stability, better crystallizability, better solubility etc., can also be administered in the form of their pharmaceutically tolerated salts.

For oral administration, the active compounds of the invention can be mixed with a diluent or ingestible vehicle, enclosed in gelatin capsules, or compressed to form tablets. For oral therapeutic administration, the active compounds can be incorporated in vehicles and used in the form of tablets, pastilles, capsules, elixirs, suspensions, syrups, wafers, chewing gum etc. These products should contain at least 0.5% by weight, relative to the total mixture, of active substance, but, depending on the particular form, the content can vary between 4 and 70% of the weight of the unit. The amount of active compound in these types of products is such that a suitable dosage can be achieved. Preferred mixtures and products contain between 10 and 300 milligrams of the active compound per single oral dose.

The tablets, pills, capsules, pastsilles etc. can additionally contain the following constituents: binders, such as microcrystalline cellulose, gum tragacanth or gelatin; vehicles, such as starch or lactose, disintegrants, such as alginic acid, maize starch etc., lubricants, such as magnesium stearate or colloidal silica, sweeteners, such as sucrose or saccharin, or a flavoring, such as peppermint, methyl salicylate or orange flavoring. In the case of a single dose in the form of a capsule, in addition to the substances mentioned this can also contain a liquid vehicle, for example an oil. Tablets or coated tablets can also be provided with, for example, sugar, shellac or other enteric coatings. In addition to the active compound, a syrup can contain sucrose as the sweetener, certain preservatives, colorants and flavorings. The materials used for preparing the mixtures should be pharmaceutically pure and non-toxic in the amount added.

For parenteral administration, the active compounds according to the invention can be incorporated in a solution or suspension. Products of these types should contain at least 0.1% by weight of the active compound relative to the total mixture, but the content can vary between 0.5 and 30% by weight. The products contain an amount of active compound such that a suitable single dose can be obtained. The mixtures and products according to the invention preferably contain between 10 and 500 mg of active substance per unit parenteral dose.

The solutions and suspensions can contain the following components: a sterile diluent, such as water for injections, saline, non-volatile oils, polyethylene glycol, glycerol, propylene glycol or other synthetic solvents, antibacterial agents, such as benzyl alcohol; antioxidants, such as ascorbic acid or sodium bisulfite; chelating agents, such as ethylenediaminetetraacetic acid; buffers, such as acetates, citrates or phosphates, and agents for adjusting the tonicity, such as sodium chloride or dextrose. The parenteral products can be dispensed into ampoules, disposable syringes or multiple-dose vials made of glass or plastic.

The example which follows illustrates the invention.

EXAMPLE 1

5-(4-Chloro-3-sulfamoylbenzoyl)-6,7-dichloro-2,3-dihydro-2-benzofurancarboxylic acid (a)

4-Allyloxy-3'-dimethylaminomethyleneaminosulfonyl-2,3,4'-trichlorobenzophenone 5.6 g (40 mmol) of allyl bromide are added dropwise, with magnetic stirring, to a mixture of 13.1 g (30 mmol) of 4-hydroxy-3'-dimethylaminomethyleneaminosulfonyl-2,3,4'-trichlorobenzophenone, 5.0 g (36 mmol) of ground potassium carbonate and 50 ml of dry dimethylformamide at room temperature, and the mixture is stirred for about 8 hours. The pale yellow suspension is then stirred in portions into a mixture of 400 ml of ice-water and 100 ml of 2N hydrochloric acid, and the precipitate is filtered off. Colorless crystals, melting point 141°–142° C. (from acetone/ethanol).

(b) 5-Allyl-4-hydroxy-3'-dimethylaminomethyleneaminosulfonyl-2,3,4'-trichlorobenzophenone 16.5 g (35 mmol) of 4-allyloxy-3'-dimethylaminomethyleneaminosulfonyl-2,3,4'-trichlorobenzophenone in 200 ml of diphenyl ether are heated at 210° to 215° C. for 1 hour, and the still warm mixture is poured in portions, with stirring, into 1.2 l of petroleum ether. The precipitate is filtered off, washed several times with petroleum ether and recrystallized from methanol. Colorless crystals, melting point 190°–193° C.

(c) 6,7-Dichloro-5-(4-chloro-3-dimethylaminomethyleneaminosulfonylbenzoyl)-2,3-dihydro-2-hydroxymethylbenzofuran 14.7 g (31 mmol) of 5-allyl-4-hydroxy-3'-dimethylaminomethyleneaminosulfonyl-2,3,4'-trichlorobenzophenone are suspended, with exclusion of moisture, in 60 ml of methylene chloride and, while cooling in an icebath, a solution of 7.4 g (43 mmol) of 90% pure metachloroperbenzoic acid in 60 ml of methylene chloride is added dropwise. The mixture is stirred for about one hour in the icebath and then briefly heated to 35° to 40° C., whereupon a clear solution is obtained. After allowing to stand at room temperature overnight, a further 0.7 g of metachloroperbenzoic acid is added, the mixture is stirred at room temperature for 4 hours and then again heated to 35° C. The precipitate is filtered off, washed twice with 10 ml of methylene chloride each time, and then washed several times with aqueous sodium bicarbonate solution until the reaction is alkaline. The organic phase is dried over sodium sulfate, the solvent is distilled off, and the amorphous product is purified by chromatography on silica gel using toluene-/ethyl acetate (3:1 to 1:3). After distilling off the solvent and recrystallizing from a little methanol, colorless crystals of melting point 180°–182° C. are obtained.

(d) 5-(4-Chloro-3-sulfamoylbenzoyl)-6,7-dichloro-2,3-dihydro-2-benzofurancarboxylic acid 1.97 g (4 mmol) of 6,7-dichloro-5-(4-chloro-3-dimethylaminomethyleneaminosulfonylbenzoyl)-2,3-dihydro-2-hydroxymethyl-benzofuran are dissolved, with exclusion of moisture and under an inert gas atmosphere, in 10 ml of anhydrous dimethylformamide, and 5.3 g (14 mmol) of pyridinium dichromate are added. The dark red solution is stirred at room temperature for one day. After addition of a further gram of pyridinium dichromate, the mixture is again allowed to stir at room temperature for 24 hours, then poured into 0.5N HCl, and this is extracted several times with ethyl acetate, and the combined organic phases are washed several times with dilute hydrochloric acid and water. After drying over sodium sulfate and distilling out the solvent, the product, which contains much chromate, is chromatographed on silica gel using a mixture of methylene chloride/cyclohexane/glacial acetic acid/ethanol 10:6:1:2. The 5-(4-chloro-3-dimethylaminoethyleneaminosulfonylbenzoyl)-6,7-dichloro-2,3-dihydro-2-benzofurancarboxylic acid obtained after evaporating off the solvent is, without further purification, heated in a mixture of 2 ml of glacial acetic acid, 0.5 ml of concentrated hydrochloric acid and 1 ml of water on a steambath for 6 hours, and then cooled in an icebath. The precipitate is filtered off and recrystallized from glacial acetic acid/water using active charcoal. Colorless crystals, melting point 218°–222° C.

We claim:

1. A 5-(4-Chloro-3-sulfamoylbenzoyl)-2,3-dihydro-2-benzofurancarboxylic acid of the formula I

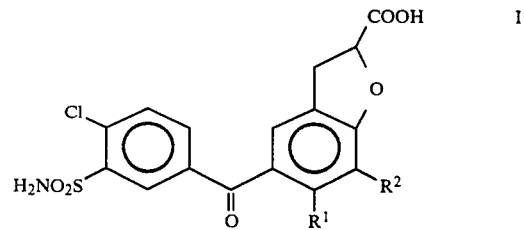

in the form of a racemic mixture or an optical isomer, in which R1 and R2 are identical or different and represent hydrogen, halogen or methyl, and its physiologically tolerated salts.

2. A compound according to claim 1 which is 5-(4-Chloro-3-sulfamoylbenzoyl)-6,7-dichloro-2,3-dihydro-2-benzofurancarboxylic acid.

3. A pharmaceutical composition having diuretic, saluretic and uricosuric activity comprising an effective amount of a compound as claimed in claim 1 and a pharmaceutically acceptable carrier.

* * * * *